(12) United States Patent
de la Rama et al.

(10) Patent No.: US 8,206,404 B2
(45) Date of Patent: Jun. 26, 2012

(54) MAGNETICALLY GUIDED CATHETER

(75) Inventors: Alan de la Rama, Cerritos, CA (US);
Kirk Kochin Wu, Walnut, CA (US);
Yongxing Zhang, Irvine, CA (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 982 days.

(21) Appl. No.: 12/167,736

(22) Filed: Jul. 3, 2008

(65) Prior Publication Data

US 2009/0012517 A1    Jan. 8, 2009

Related U.S. Application Data

(60) Provisional application No. 60/947,791, filed on Jul. 3, 2007.

(51) Int. Cl.
*A61B 19/00* (2006.01)
*A61B 18/18* (2006.01)
*A61M 25/00* (2006.01)

(52) U.S. Cl. .................... 606/129; 606/41; 604/528

(58) Field of Classification Search ............... 606/29, 606/41, 129, 130, 34; 600/374, 114, 146; 604/528

See application file for complete search history.

(56) References Cited

U.S. PATENT DOCUMENTS

| | | |
|---|---|---|
| 3,674,014 A | 7/1972 | Tillander |
| 4,809,713 A | 3/1989 | Grayzel |
| 4,945,912 A | 8/1990 | Langberg |
| 5,056,517 A | 10/1991 | Fenici |
| 5,279,299 A | 1/1994 | Imran |
| 5,363,861 A | 11/1994 | Edwards et al. |
| 5,542,938 A | 8/1996 | Avellanet et al. |
| 5,545,200 A | 8/1996 | West et al. |
| 5,706,827 A | 1/1998 | Ehr et al. |
| 5,782,810 A | 7/1998 | O'Donnell |
| 5,788,713 A | 8/1998 | Dubach et al. |
| 5,911,720 A | 6/1999 | Bourne et al. |
| 6,015,414 A | 1/2000 | Werp et al. |
| 6,126,647 A | 10/2000 | Posey et al. |
| 6,185,448 B1 | 2/2001 | Borovsky |
| 6,235,024 B1 | 5/2001 | Tu |
| 6,273,876 B1 | 8/2001 | Klima et al. |
| 6,292,678 B1 | 9/2001 | Hall et al. |
| 6,356,790 B1 | 3/2002 | Maguire et al. |
| 6,385,472 B1 | 5/2002 | Hall et al. |

(Continued)

FOREIGN PATENT DOCUMENTS

WO    WO-96/34652    11/1996

(Continued)

*Primary Examiner* — Jackie Ho
*Assistant Examiner* — Leah Stohr
(74) *Attorney, Agent, or Firm* — Armstrong Teasdale LLP (57) ABSTRACT

A catheter includes a flexible tubing having a proximal end and a distal end. The catheter also includes an electrode assembly attached to the distal end of the flexible tubing and having a first magnet therein. The electrode assembly further includes an electrically conductive tip electrode and an electrically nonconductive coupler which is connected between the tip electrode and the distal end of the flexible tubing. The coupler and the tip electrode are coupled by an interlocking connection. The catheter also includes a second magnet spaced from the electrode assembly along a longitudinal axis of the tubing. The first magnet and the second magnet are responsive to an external magnetic field to selectively position and guide the electrode assembly within a body of a patient.

29 Claims, 7 Drawing Sheets

U.S. PATENT DOCUMENTS

| | | |
|---|---|---|
| 6,475,223 B1 | 11/2002 | Werp et al. |
| 6,493,590 B1 | 12/2002 | Wessman et al. |
| 6,524,303 B1 | 2/2003 | Garibaldi |
| 6,544,270 B1 | 4/2003 | Zhang |
| 6,662,034 B2 | 12/2003 | Segner et al. |
| 6,669,692 B1 | 12/2003 | Nelson et al. |
| 6,690,963 B2 | 2/2004 | Ben-Haim et al. |
| 6,730,082 B2 | 5/2004 | Messing et al. |
| 6,733,497 B2 | 5/2004 | Messing et al. |
| 6,740,083 B2 | 5/2004 | Messing et al. |
| 6,755,816 B2 | 6/2004 | Ritter et al. |
| 6,980,843 B2 * | 12/2005 | Eng et al. .................. 600/374 |
| 7,211,082 B2 | 5/2007 | Hall et al. |
| 7,276,044 B2 | 10/2007 | Ferry et al. |
| 7,341,063 B2 | 3/2008 | Garibaldi et al. |
| 7,815,635 B2 * | 10/2010 | Wittkampf et al. ............. 606/41 |
| 2002/0058866 A1 | 5/2002 | Segner et al. |
| 2002/0072662 A1 | 6/2002 | Hall et al. |
| 2003/0125752 A1 | 7/2003 | Werp et al. |
| 2003/0176786 A1 | 9/2003 | Maschke |
| 2004/0015215 A1 | 1/2004 | Fredricks et al. |
| 2004/0158142 A1 | 8/2004 | Hall et al. |
| 2004/0231683 A1 | 11/2004 | Eng et al. |
| 2004/0242995 A1 | 12/2004 | Maschke |
| 2004/0243143 A1 | 12/2004 | Corcoran et al. |
| 2004/0267106 A1 * | 12/2004 | Segner et al. .................. 600/374 |
| 2005/0245846 A1 | 11/2005 | Casey |
| 2006/0064123 A1 | 3/2006 | Bonnette et al. |
| 2006/0116633 A1 | 6/2006 | Shachar |
| 2007/0016006 A1 | 1/2007 | Shachar |
| 2007/0066878 A1 | 3/2007 | Worley et al. |
| 2007/0073288 A1 | 3/2007 | Hall et al. |

FOREIGN PATENT DOCUMENTS

| | | |
|---|---|---|
| WO | WO-2005/094661 | 10/2005 |

* cited by examiner

MAGNETICALLY GUIDED CATHETER

CROSS REFERENCE TO RELATED APPLICATIONS

This application claims the benefit of U.S. Provisional Application No. 60/947,791, filed Jul. 3, 2007, which is hereby incorporated by reference in its entirety.

BACKGROUND OF THE INVENTION

This invention relates generally to medical instruments, and, more specifically, to a navigable catheter device positionable within a body of a patient using an externally applied magnetic field.

Catheters are flexible, tubular devices that are widely used by physicians performing medical procedures to gain access into interior regions of the body. Careful and precise positioning of the catheters within the body is important to successfully completing such medical procedures. This is particularly so when catheters are used to produce emissions of energy within the body during tissue ablation procedures. Conventionally, positioning of such catheters was accomplished with mechanically steerable devices. More recently, magnetically navigable catheter devices have been developed that may be navigated with an externally applied magnetic field. Such catheter devices can be complex in their construction, and therefore are difficult to manufacture and relatively expensive to produce.

Magnetic stereotactic systems have been developed that are particularly advantageous for positioning of catheters, as well as other devices, into areas of the body that were previously inaccessible. Such systems utilize computer controlled superconducting coils to generate specific magnetic fields or gradients to move a catheter that is provided with magnetic components responsive to such magnetic fields. The magnetic fields and gradients are generated to precisely control the position of the catheter within the patient's body. Once correctly positioned, physicians may operate the catheter, for example, to ablate tissue to clear a passage in the body. Specifically, such stereotactic systems monitor the position of a tip of the catheter in response to the applied magnetic fields of the superconducting coils, and using well established feedback and control algorithms the catheter tip may be guided to and positioned in a desired location within the patient's body.

The magnetic response of the catheter can be a limitation on the precise control of a catheter when used with such magnetic guidance systems. Improvements in catheters utilized with magnetic guidance and control systems, such as stereotactic systems, are desired. Specifically, a low cost, yet high performance magnetically guided catheter is desirable.

BRIEF DESCRIPTION OF THE INVENTION

In various embodiments, magnetic guided catheters are disclosed that are manufacturable at relatively low cost while providing high performance when used with, for example, magnetic stereotactic systems.

In one embodiment, a catheter is provided that includes a flexible tubing having a proximal end and a distal end. The catheter also includes an electrode assembly attached to the distal end of the flexible tubing and having a first magnet therein. The electrode assembly further includes an electrically conductive tip electrode and an electrically nonconductive coupler which is connected between the tip electrode and the distal end of the flexible tubing. The coupler and the tip electrode are coupled by an interlocking connection. The catheter also includes a second magnet spaced from the electrode assembly along a longitudinal axis of the tubing. The first magnet and the second magnet are responsive to an external magnetic field to selectively position and guide the electrode assembly within a body of a patient.

In another embodiment, a catheter is provided that includes an electrode assembly attached to the distal end of the flexible tubing and including a first magnet therein. The electrode assembly including an electrically conductive tip electrode and an electrically nonconductive coupler which is connected between the tip electrode and the distal end of the flexible tubing. The catheter further includes a second magnet spaced from the electrode assembly along a longitudinal axis of the tubing. The flexible tubing is a unitary tubing, and the second magnet is placed inside the flexible tubing after the unitary flexible tubing is formed. The first magnet and the second magnet are responsive to an external magnetic field to selectively position and guide the electrode assembly within a body of a patient.

DETAILED DESCRIPTION OF THE INVENTION

Many specific details of certain embodiments of the invention are set forth in the following description in order to provide a thorough understanding of such embodiments. One skilled in the art, however, will understand that the present invention may have additional embodiments, or that the present invention may be practiced without several of the details described in the following description.

Figure 1:
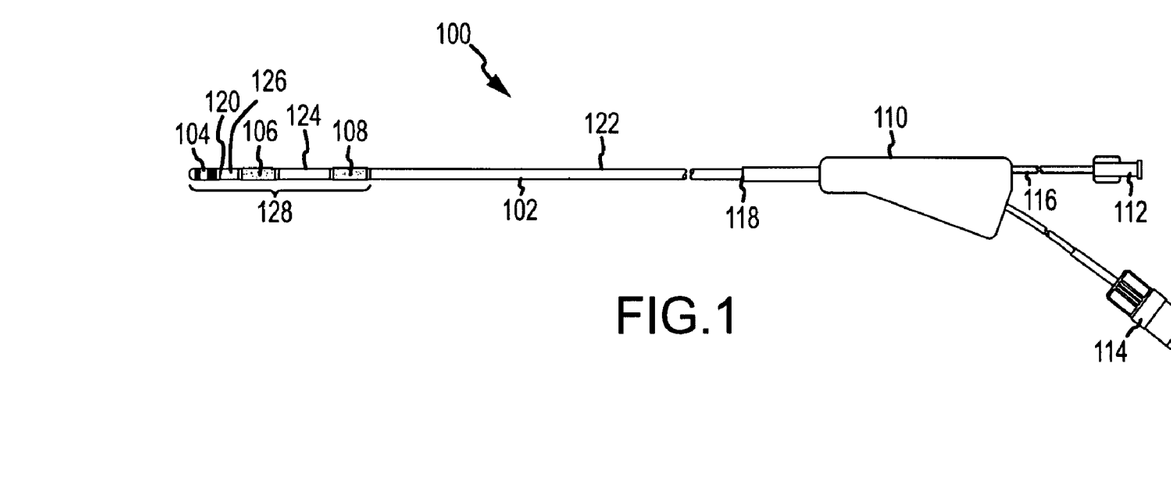
FIG. 1 illustrates a first exemplary magnetic guided catheter.

FIG. 1 illustrates a first exemplary non-steerable, single-use magnetically guided catheter 100 generally including a flexible outer tube, or tubing, 102, a tip assembly 104, positioning magnets 106 and 108 separately provided from and spaced from tip assembly 104, a Y connector 110, a luer device 112, and an electrical connector 114. Luer device 112 is used to open or close a flow path so that fluid is passed through Y-connector 110 and tubing 102 to tip assembly 104 for irrigation purposes. Electrical connector 114 establishes electrical connection with a power source (not shown) that operates electrodes of tip assembly 104 to perform, for example, ablation procedures, mapping or pacing procedures, or to perform other aspects of a medical procedure.

Although it will become evident that aspects of exemplary catheter 100 are applicable to a variety of medical procedures and end uses, the invention will be described principally in the context of a specific example of a magnetically guided catheter. Specifically, catheter 100, as shown in FIG. 1, is believed to be particularly advantageous as an ablation catheter for creating endocardial lesions during cardiac ablation procedures to treat arrhythmias, and also for cardiac electrophysiological mapping and delivering diagnostic pacing stimuli. However, the invention and the appended claims are not intended to be limited to any specific example, including but not limited to specific examples or embodiments described herein, except when explicitly defined as such in the appended claims.

Y-connector 110 separates an inner tube 116 from electrical lead wires (not shown) extending between tip assembly 104 and electrical connector 114. More specifically, tube 116 and the lead wires forward of Y-connector 110 pass internally through outer tube 102, while aft of Y-connector 110, inner tube 116 and leads for the lead wires are exposed and separated for connection to a fluid source (not shown) and the power source, respectively. In one embodiment, electrical connector 114 is a known connector configured to engage the power source or a power supply with, for example, a plug-in connection. One suitable electrical connector is a 14 pin REDEL® plastic connector commercially available from LEMO of Rohnert Park, Calif., although other connectors from various manufacturers may likewise be utilized.

Outer tube 102 includes a proximal end 118 coupled to Y-connector 110, a distal end 120 coupled to tip assembly 104, and an axial length extending between proximal end 118 and distal end 120. In one embodiment, flexible tubing 102 is fabricated according to known processes, such as extrusion processes, from any suitable tubing material known in the art of medical instruments, such as engineered nylon resins and plastics, including but not limited to PEBAX® tubing of Ato Fina Chemicals, France.

In an exemplary embodiment tubing 102 is fabricated from a first tubing material defining a first portion 122 of tubing 102 between Y connector 110 and magnet 108, a second tubing material defining a second portion 124 of tubing 102 between magnet 106 and magnet 108, and a third tubing material defining a third portion 126 of tubing 102 extending between magnet 106 and tip assembly 104. In an exemplary embodiment, first portion 122, second portion 124 and/or third portion 126 are fabricated from different materials and grades of materials for enhanced performance of tubing 102 in use of catheter assembly 100. Tubing 102, by virtue of portions 122, 124, and 126 having varying flexible properties, is sometimes referred to as a multi-flexible tube.

For example, in one embodiment, the first material defining first portion 122 of tubing 102 is a comparatively rigid and kink resistant braided material. First portion 122 is formed with different portions of braided material, semi-soft material, and soft material fused to one another so that first portion 122 becomes increasingly flexible along the axial length as first portion 122 approaches magnet 108. The second material defining second portion 124 of tubing 102, and the third material defining third portion 126 of tubing 102 is a soft and flexible material having approximately equal flexible properties. In the illustrated embodiment, each of tubing portions 122, 124, and 126 between tip assembly 104 and magnets 106 and 108 share a common outside diameter of, for example, 7 French, although in other embodiments, tubing portions 122, 124 and 126 have varied diameters.

As shown in FIG. 1, first portion 122 extends for a majority of the axial length of tubing 102 between proximal end 118 and distal end 120. Second portion 124 of tubing 102 extends for a shorter length than the length of first portion 122, and third portion 126 of tubing 102 extends for a length that is shorter than the length of second portion 124. By way of example only, in a specific embodiment first portion 122 extends for an axial length of about 126.3 cm, second portion 124 extends for an axial length of about 2.2 cm, and third portion 126 extends for an axial length of about 0.8 cm, although other relative lengths of the tube portions may likewise be employed in other embodiments. The different relative lengths of tube portions 122, 124 and 126, as well as the different flexible properties of tube portions 122, 124 and 126, allow tip assembly 104 to be more precisely positioned within a patient's body, while also avoiding problems of kinks and excessive deflection of tubing 102 along the majority of its length during use and handling.

As another consequence of tubing sections 124 and 126 having an unequal length, magnet 106 is spaced a first distance from tip assembly 104, and magnet 108 is spaced a second, greater distance from magnet 106 since tubing portion 124 is longer than tubing portion 126. Due to the spacing of magnets 106 and 108 relative to one another and also to tip assembly 104, which as explained below also includes a positioning magnet (not shown in FIG. 1), the spacing of magnets 106 and 108 permits positioning adjustment of tip assembly 104 in response to variations in an externally applied magnetic field that may otherwise not be possible, if magnets 106 and 108 were provided in an equal or uniform spaced relation to one another. It is contemplated, however, that in another embodiment tip assembly 104, magnet 106 and magnet 108 are equally spaced from one another.

In operation, a distal end portion 128 of catheter 100 including tip assembly 104 is navigated to a site in the body where a medical procedure, such as an atrial mapping, pacing and/or ablation are to occur. Distal end portion 128 may extend, for example, into a heart chamber of a patient. Once distal end portion 128 is in the heart chamber, a magnetic field is applied to provide an orienting force to distal end portion 128, causing the tip positioning magnet and magnets 106 and 108 to respond to the applied magnetic field and flex tubing portions 124 and 122 to precisely position tip assembly 104 for performance of the procedure at a specific location. The magnetic fields used to orient tip assembly 104 are, in one embodiment, generated with a magnetic stereotactic system (not shown). Such stereotactic systems are known and are commercially available from, for example, Stereotaxis of St. Louis, Mo. Such systems may include movable source magnets outside the body of the patient, and operative details of such systems are disclosed in, for example, U.S. Pat. Nos. 6,475,223 and 6,755,816, the disclosures of which are hereby incorporated by reference in their entirety. While catheter 100 is advantageous for use with a stereotactic system, it is contemplated that magnetic fields and gradients to deflect catheter tip assembly 104 may alternatively be generated by other systems and techniques if desired.

Figure 2:
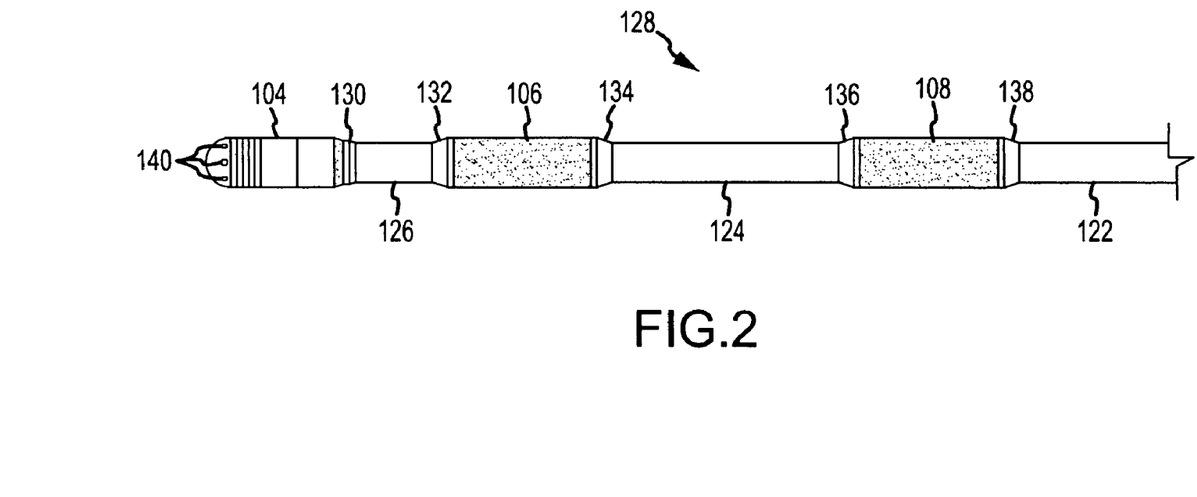
FIG. 2 is a magnified view of a distal end portion of the catheter shown in FIG. 1.

FIG. 2 is a magnified view of distal end portion 128 of catheter 100 shown in FIG. 1. Tip assembly 104 is coupled to a first end 130 of tube portion 126 and magnet 106 is coupled to a second end 132 of tube portion 126. A first end 134 of tube portion 124 is coupled to magnet 106 and a second end 136 of tube portion 124 is coupled to magnet 108. A first end 138 of tube portion 122 is coupled to magnet 108, and a second end (not shown in FIG. 2) of tube portion 122 is coupled to connector 110 (shown in FIG. 1). As shown in FIG. 2, tip assembly 104 includes irrigation ports or openings 140 for passage of fluid from within tubing 102 (shown in FIG. 1) to an exterior of tip assembly 104 when located in the body of a patient.

Figure 3:
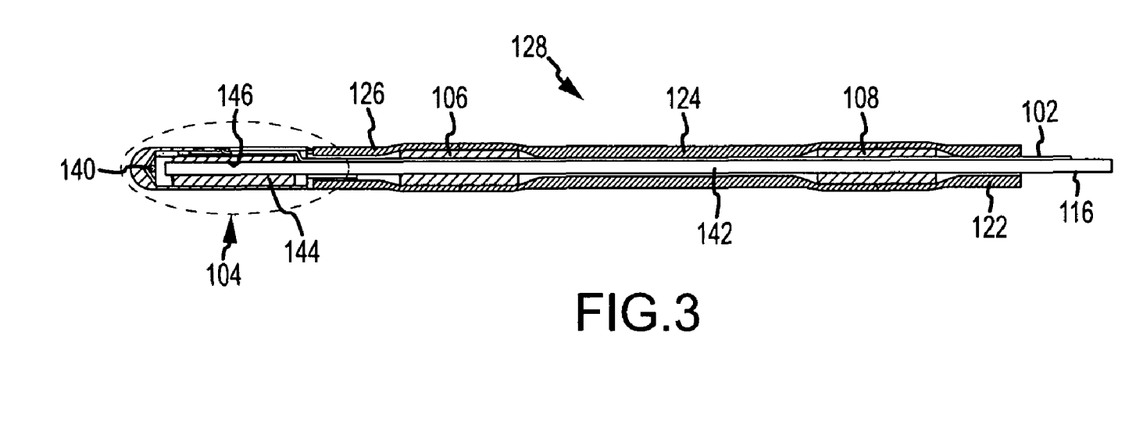
FIG. 3 is a cross sectional view of the distal end portion shown in FIG. 2.

FIG. 3 is a cross sectional view of distal end portion 128 wherein inner tube 116 defines a central lumen 142 extending through each tube portion 122, 124, and 126, and also through central bores formed in magnets 106 and 108. Inner tube 116 has an outer diameter that is smaller than an inner diameter of tubing 102 and its portions 122, 124, and 126 such that space extends between an outer surface of inner tube 116 and an inner surface of tubing 102. In one embodiment, this space is used to accommodate lead wires for electrical components of tip assembly 104.

Tip assembly 104 also includes a positioning magnet 144 having an internal bore 146 passing therethrough. Inner tube 116 passes through central bore 146 in magnet 144. Central lumen 142 is in fluid communication with luer 112 (shown in FIG. 1) on one end and with irrigation ports 140 extending through tip assembly 104 at the other end. Thus, an irrigation fluid, such as saline, may be injected through distal end portion 128. Inner tube 116 may be, for example, a braided polyimide tube that maintains the flowpath through lumen 142 in all orientations of tip assembly 104, without compromising the flexibility of tubing 102.

Figure 4:
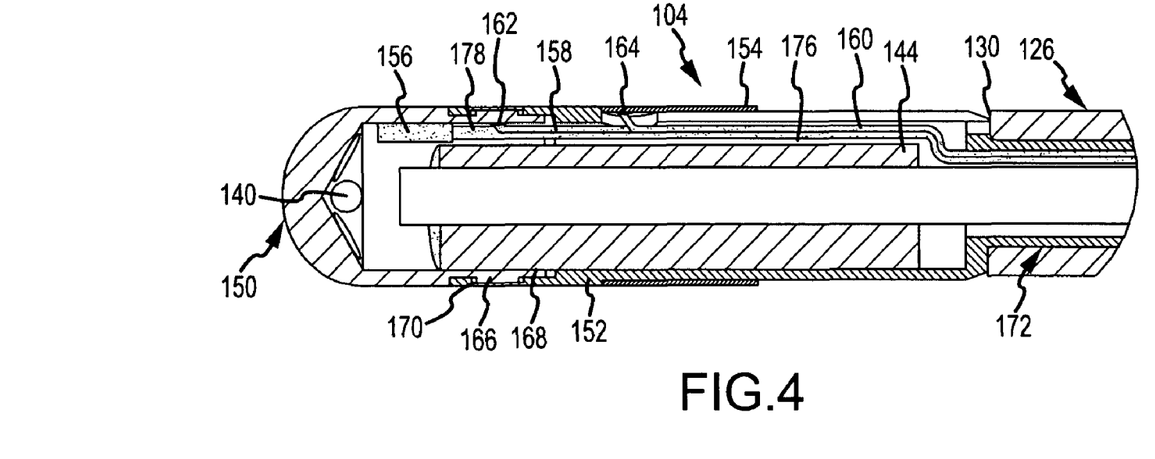
FIG. 4 is a magnified cross sectional view of the electrode tip assembly shown in FIGS. 2 and 3.

FIG. 4 is a magnified cross sectional view of tip assembly 104. In an exemplary embodiment tip assembly 104 includes a tip electrode 150, a coupler 152, a band electrode 154, positioning magnet 144, and a temperature sensor 156. Lead wires 158, 160 extend to tip electrode 150, and to band electrode 154 on first respective ends 162, 164 thereof, and to connector 114 (shown in FIG. 1) on second ends (not shown) so that electrodes 150 and 154 may be energized by a power source (not shown).

In the exemplary embodiment, tip electrode 150 may be, for example an 8 Fr hemispherical-shaped tip electrode that is 2 mm in length. In other embodiments, other sizes of tip electrodes may be utilized, including but not limited to 4 mm or 8 mm tip electrodes. Tip electrode 150 is formed with a plurality of openings that form irrigation ports 140 for saline irrigation. In the exemplary embodiment, tip electrode 150 is fabricated from 90% platinum and 10% iridium, or other materials known in the art such that tip electrode 150 is viewable under fluoroscopic exposure. While formed as an integral unit, tip electrode 150 may include multiple electrode elements, such as ring electrodes for electrophysiological mapping purposes, spaced from one another by dielectric materials as is known in the art.

Coupler 152 is a generally cylindrical, electrically nonconductive member. It is typically made of a polymer such as PEEK™, which is relatively rigid compared to rubber and has a limited amount of flexibility and resiliency to form a snap-fit connection, for example. Tip electrode 150 is formed with an annular projection 166 on its outer surface that engages a groove 168 within a first end 170 of coupler 152 to form a snap-fit, interlocking connection. Alternatively, any mating configuration of tip assembly 104 and coupler 152 may be used. Coupler 152 includes a second end 172 that is fitted within first end 130 of tube portion 126. Additionally, or alternatively thereto, first end 170 of coupler 152 is adhered to tip electrode 150. Second end 172 of coupler 152 is adhered to the inner diameter of tube portion 126. Heat shrink techniques or adhesives may also be utilized to permanently attach coupler 152 to tube portion 126 and/or tip electrode 150. Positioning magnet 144 is disposed in a cavity which is formed at least partially inside the coupler 152 and which may be formed partially inside coupler 152 and partially inside tip electrode 150. Coupler 152 houses positioning magnet 144 in tip assembly 104 and supports optional band electrode 154, is more rigid than flexible tubing 102, and provides a convenient and reliable connection between tip electrode 150 and third portion 126 of flexible tubing 102.

Band electrode 154 is, in one embodiment, an 8 Fr ring-shaped band electrode that is for example, 2 mm in length, and spaced from tip electrode 150 by a predetermined distance of 2 mm. Band electrode 154 is, in one embodiment, fabricated from the same material as or a different material from tip electrode 150 and is attached to an outer surface of coupler 152.

In one embodiment, tip positioning magnet 144 is a generally cylindrical shaped permanent magnet fabricated from a known magnetic material, such as neodymium-iron boron— 45 (NdFeB-45). Alternatively, magnet 144 is formed from other materials and may have shapes different from the elongated cylindrical shape illustrated.

As shown in FIG. 4, magnet 144 includes an axially extending recess, or groove, 176 formed into an exterior of magnet 144. Lead wires 158, 160, and a lead wire 178 for temperature sensor 158 pass through recess 176 in a space defined by recess 176 and an inner surface of coupler 152. Temperature sensor 158 is, in one embodiment, a thermocouple type temperature sensor, and lead wires 158, 160, and 178 are, for example, 38 AWG wires having quad polyimide insulation.

Tip assembly 104 is particularly suited for ablation procedures wherein electrodes 150 and 154 are energized to deliver radio frequency waves at the site of an abnormal electrical pathway in the body. Radiofrequency (RF) energy may therefore be applied to biological tissue in proximity to tip assembly 104. Ablation procedures are typically used, for example, within the interior chambers of the heart to thermally ablate cardiac tissue. Electrodes 150 and 154 may additionally be operated to record intracardiac signals and to provide pacing signals.

Figure 5:
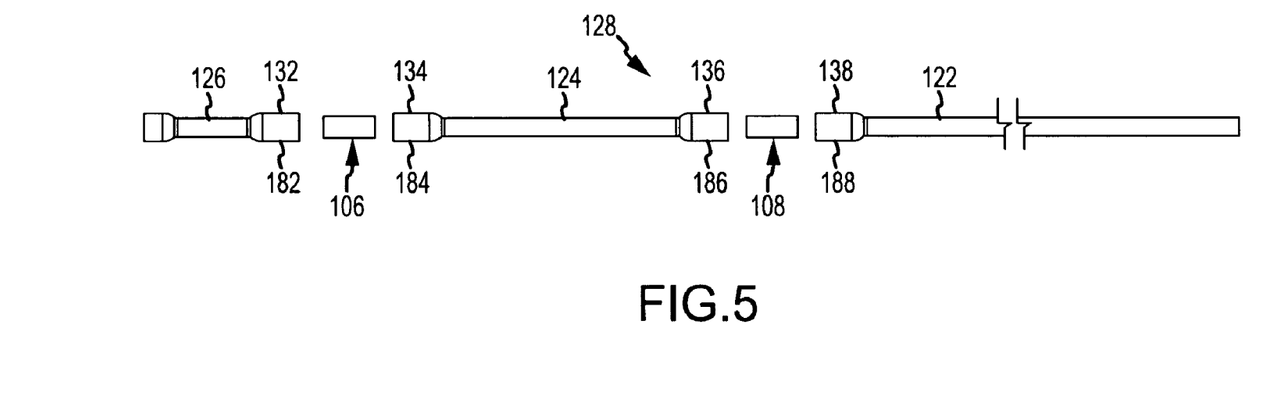
FIG. 5 is an exploded view of the distal end portion shown in FIG. 2 of the catheter shown in FIG. 1.

FIG. 5 is an exploded view of catheter distal end portion 128 (shown in FIG. 1). Magnets 106 and 108 are each permanent magnets formed from, for example, neodymium-iron boron—45 (NdFeB-45) into an elongated tubular shape.

As shown in FIG. 5, second end 132 of tube portion 126, first and second ends 134, 136 of tube portion 124, and first end 138 of tube portion 122 are formed into outwardly flared sockets 182, 184, 186 and 188. Magnet 106 is received in socket 182 of tube second end 132 and socket 184 of tube portion first end 134. Magnet 108 is received in socket 186 of tube portion second end 136 and socket 188 of tube portion first end 138. In the exemplary embodiment, sockets 182, 184, 186, and 188 are formed with a flaring tool and extend, for example, an axial length of about 2.5 mm. Sockets 182, 184, 186, and 188 are, in the exemplary embodiment, adhered to magnets 106 and 108, respectively, and heat shrunk to fuse sockets 182 and 184 to magnet 106 and sockets 186 and 188 to magnet 108. In another embodiment, sockets 182, 184, 186, and 188 are maintained in position with a friction fit. In the exemplary embodiment, adjacent tube ends 132 and 134 as well as adjacent tube ends 136 and 138 contact each other and, in a particular embodiment, are fused to each other.

Tube portions 122, 124, and 126 have an outer diameter, at locations other than sockets 182, 184, 186, and 188, that is smaller than the outer diameter of tube portions 122, 124, and 126 at the location of sockets 182, 184, 186, and 188. In one embodiment, the outer diameter of magnets 106 and 108 is the same as, or larger than, the outer diameter of tube portions 122, 124, and 126 at locations other than sockets 182, 184, 186, and 188. The larger diameter magnets are able to provide an enhanced response for positioning of catheter 100 (shown in FIG. 1) with externally applied magnetic fields.

Figure 6:
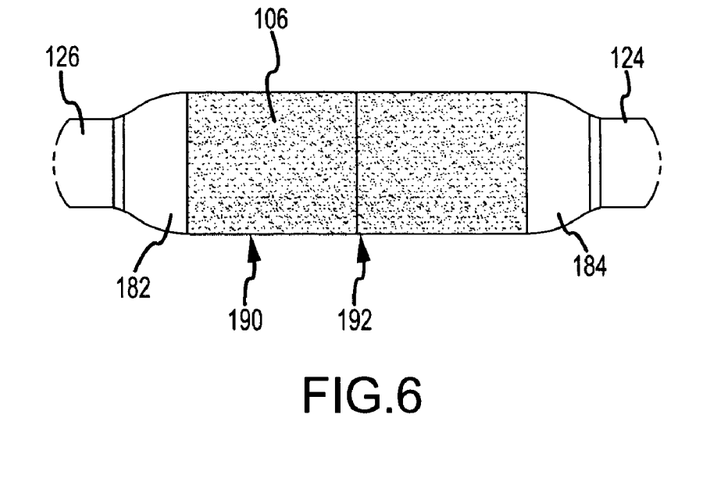
FIG. 6 illustrates an enlarged view of an alternate connecting structure for the attachment of the tube portions to the magnets.

FIG. 6 illustrates an enlarged view of an alternate connecting structure for the attachment of tube portions 126 and 124 to magnet 106. As shown in FIG. 6, a sleeve member 190 extends over sockets 182 and 184 and forms a smooth outer surface for a transition 192 from tube portion 126 over magnet 106 to tube portion 124. Sheath 190 is, in one embodiment, fabricated from a thin tube of a polyimide material, or any other material that provides a low coefficient of friction.

Although only three tube portions 122, 124, and 126 and two magnets 106 and 108 spaced from tip assembly 104 are shown in FIGS. 1-6, it should be understood that fewer than, or more than three tube portions and two magnets could be used without departing from the spirit of the hereinabove described catheter.

FIGS. 7 through 11 illustrate a second exemplary embodiment of a magnetically guided catheter 200 that is similar in many aspects to catheter 100 described above. Like components and features of catheter 100 are indicated with like reference numbers in FIGS. 7 through 11. Unlike catheter 100, catheter 200 includes a distal end portion 202 that is different from tip assembly 104 described above. Distal end portion 202 includes magnets 204 and 206 (instead of magnets 106 and 108), rounded tip electrode 208, and tip element 210.

Figures 7, 8:
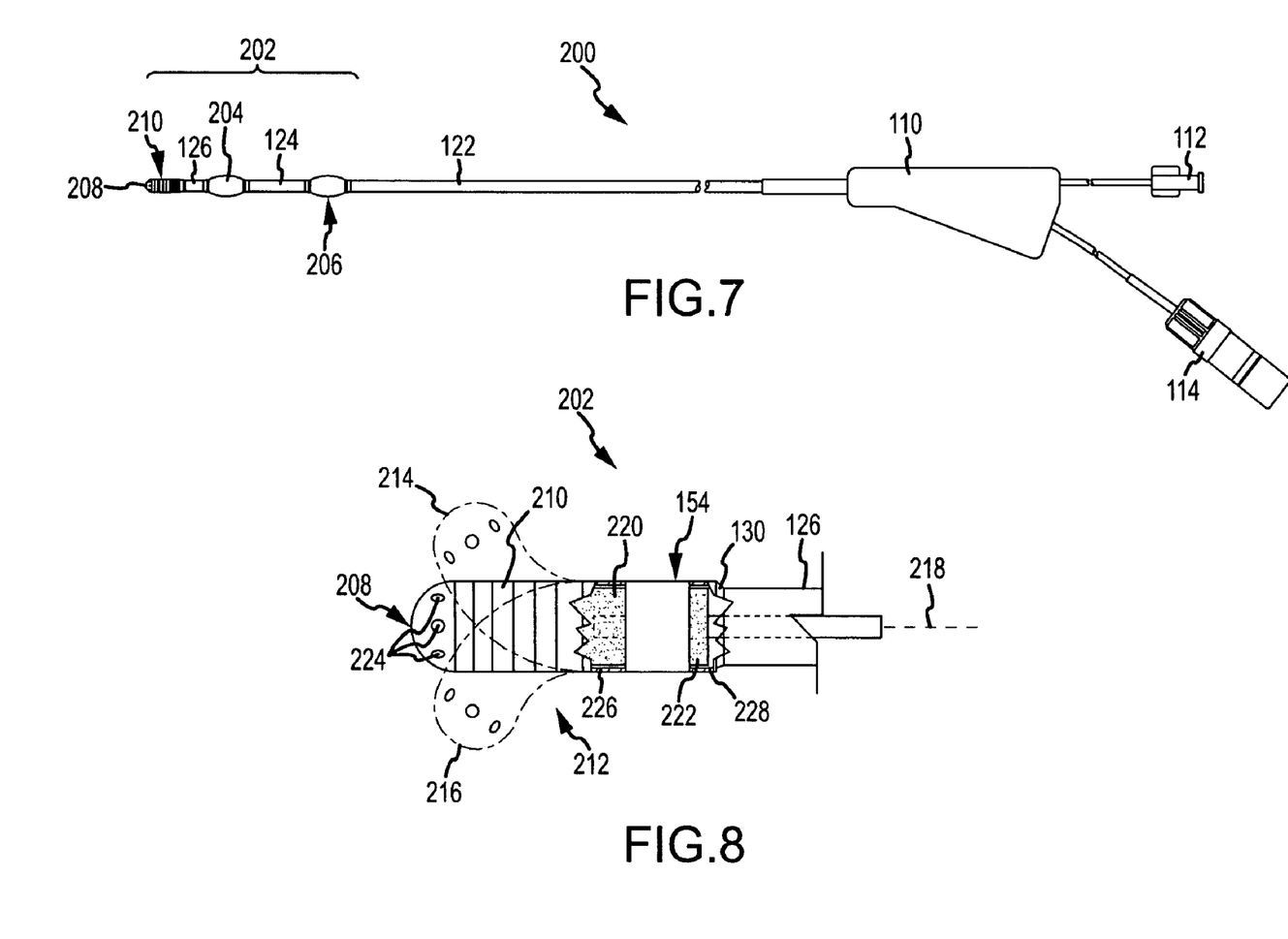
FIG. 7 illustrates a second exemplary embodiment of a magnetically guide catheter.
FIG. 8 illustrates an electrode assembly for the catheter shown in FIG. 7.

FIG. 8 illustrates distal end portion 202 including a tip assembly 212 that includes rounded tip electrode 208 and tip element 210. Tip element 210 is a flexible member that allows tip assembly 212 to flex, bend or deflect along its axial length to, for example, different operating positions 214 and 216 (shown in phantom in FIG. 8) in addition to the in-line configuration shown in solid lines in FIG. 8 wherein the tip is straight and generally linear along a longitudinal axis 218.

Tip assembly 212 also includes a coupler 220 that joins tip element 210 to tube portion 126, a band electrode 154, and a positioning magnet 222 provided internal to tip assembly 212. In the exemplary embodiment, tip electrode 208 may be, for example an 8 Fr hemispherical-shaped tip electrode that is 2 mm in length. In other embodiments, other sizes of tip electrodes may be utilized, including but not limited to 4 mm or 8 mm tip electrodes. Tip electrode 208 is formed with a plurality of openings that form irrigation ports 224 for saline irrigation. In the exemplary embodiment, tip electrode 208 is fabricated from 90% platinum and 10% iridium, or other materials known in the art such that tip electrode 208 is viewable under fluoroscopic exposure. While formed as an integral unit, tip electrode 150 may include multiple electrode elements, such as ring electrodes for electrophysiological mapping purposes, spaced from one another by dielectric materials as is known in the art.

Coupler 220 is a generally cylindrical, electrically nonconductive member. It is typically made of a polymer such as PEEK™, which is relatively rigid compared to rubber and has a limited amount of flexibility and resiliency to form a snap-fit connection, for example. Coupler 220 is connected at a first end 226 to tip element 210 and at a second end 228 to first end 130 of tube portion 126. Coupler 220 is, in one embodiment, engaged to tip element 210 with a snap-fit, interlocking engagement similar to coupler 152 in FIG. 4. Additionally, or alternatively thereto, coupler 220 is adhered to tip element 210. In addition, coupler 220 is adhered to an inner section of tube portion 126. Heat shrink techniques may also be utilized to permanently attach coupler 220 to tube portion 126 and/or tip element 210. Positioning magnet 222 is disposed in a cavity which is formed at least partially inside coupler 220 and which may be formed partially inside coupler 220 and partially inside tip element 210. Coupler 220 houses positioning magnet 222 in tip assembly 212 and supports optional band electrode 154, is more rigid than flexible tubing 102, and provides a convenient and reliable connection between tip element 210 and third portion 126 of flexible tubing 102.

Band electrode 154 is, in one embodiment, an 8 Fr ring-shaped band electrode that is for example, 2 mm in length, and spaced from tip electrode 208 by a predetermined distance of 2 mm. Band electrode 154 is, in one embodiment, fabricated from the same material as or a different material from tip electrode 150 and is attached to an outer surface of coupler 220.

In one embodiment, tip positioning magnet 222 is a generally cylindrical shaped permanent magnet fabricated from a known magnetic material, such as neodymium-iron boron—45 (NdFeB-45). Alternatively, magnet 222 is formed from other materials and may have shapes different from the elongated cylindrical shape illustrated.

Figure 9:
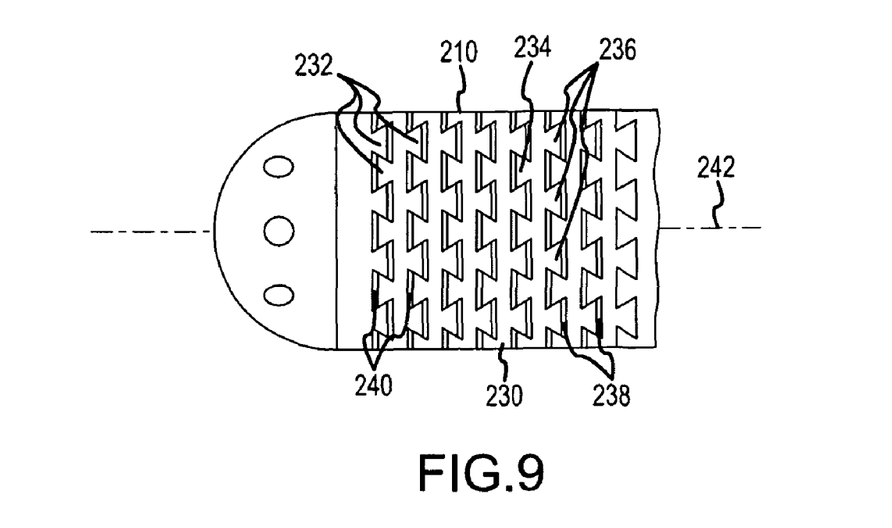
FIG. 9 is a magnified assembly view of a portion of the tip assembly shown in FIG. 8.

FIG. 9 illustrates exemplary tip element 210 in further detail. In the exemplary embodiment, tip element 210 is comprised of a single member that is formed into a helix, or spiral, and extends from tip electrode 208 to coupler 220. Tip element 210 includes a helically shaped body 230 having alternately spaced projections 232 extending away from body 230 in opposite directions from one another along the length of the helix. That is, a first set of projections 234 extends distally, i.e., towards tip electrode 208, and a second set of projections 236 extends proximally, i.e., away from tip electrode 208. The first set of projections 234 are staggered or offset from the second set of projections 236 such that the first set of projections 234 are offset from, and positioned between, the second set of projections 236.

Recesses 238 extend between projections 232 and are complementary in shape to an outer contour of projections 232, but inversely shaped from projections 232. In the illustrated embodiment, projections 232, and recesses 238, are trapezoidal in shape, although it is contemplated that other shapes could likewise be utilized in alternative embodiments.

Tip element 210 is fabricated such that projections 232 from one section of body 230 extend into, and are captured within, recesses 238 from an adjacent section of body 230 to form an interlocking arrangement. Due to projections 232 being complementary in shape to recesses 238 and thus defining sockets or compartments for projections 232, projections 232 are movable only a defined distance within recesses 238. In particular, and as shown in FIG. 9, tip element 210 is positionable to create a space or gap 240 between leading edges of projections 232 and inner edges of recesses 238. Projections 232 and recesses 238 of tip element 210 extend completely along the length of body 230 and, in one embodiment, are uniformly spaced and sized around a perimeter of body 230. Alternatively, projections 232 and recesses 238 may be differently sized and/or spaced around the perimeter of body 230.

As a consequence of gaps 240, and also the complementary shapes of projections 232 and recesses 238, projections 232 are provided a freedom of movement within recesses 254 without being able to be removed therefrom. Accordingly, sections of tip element 210 can move toward and away from each other a defined distance to decrease and increase, respectively, gaps 240. It is thus possible for sections of tip element 210 to move relative to one another in multiple ways. For example, tip element 210 may be compressed so that all of gaps 240 are closed, or nearly closed, to reduce the longitudinal length of tip assembly 202 by the cumulative dimensions of gaps 240 along a longitudinal axis 242. Additionally, sections of tip element 210 may exhibit cascaded or sequential movement along longitudinal axis 242 wherein some gaps 240 are closed along longitudinal axis 242 while other gaps 240 remain open, either partially or fully. This allows gaps 240 between any adjacent sections of tip element 210 to be opened or closed in an uneven or non-uniform manner. As such, gaps 240 on one side of tip assembly 202 may be closed while gaps 240 on the other side of tip assembly 202 may be opened. The result of this configuration is that tip assembly 202 curves in the direction of the closed gaps 240 and away from the direction of the opened gaps 240. It can be appreciated that movement in vertical and horizontal planes may simultaneously occur due to the interlocking construction of tip element 210 to flex and deflect tip assembly 202 to a practically unlimited number of positions. Tip assembly 202 may deflect in the manner described due to, for example, impact forces on an outer surface of tip assembly 202 in use, and may also, in whole or in part, be the result of the magnetic response of positioning magnet 222 (shown in FIG. 8) and magnets 204 and 206 (shown in FIG. 7).

In an exemplary embodiment, tip element 210 is laser cut from a material suitable for surgical use, such as an electrically conductive, non-corrosive material. In one exemplary embodiment, the material is platinum. In another exemplary embodiment, the material is stainless steel. Projections 232 and recesses 238 of tip element 210 are, in the exemplary embodiment, laser cut out of a cylindrical piece of material. It should be evident that as the number of helices increases in tip element 210, the flexing capability also increases. In addition, as the pitch of the helix decreases, the ability of tip element 210 to move relative to itself increases. The flexibility may further be adjusted by providing different numbers and shapes of projections and recesses to produce tip assemblies that flex to varying degrees to meet different objectives. The combination of the multi-flexing tubing previously described and independent flexing of the tip assembly 212 is particularly advantageous for certain applications. For example, RF energy may be more specifically targeted to desired tissue areas for ablation procedures when tip element 212 is flexed than when it is not flexed, and provides a physician with additional positioning capability over conventional catheter devices.

In an alternative embodiment, tip assembly includes a plurality of adjacent rings that extend along longitudinal axis 242. Each ring has a distal side and a proximal side and each side includes alternating projections and recesses. This structure provides for flexibility in a manner that is similar to the exemplary embodiment described above. In such a configuration, the rings are constructed substantially identically to each other.

Tip assembly 212 is particularly suited for ablation procedures wherein electrode 208 is energized to deliver radio frequency waves at the site of an abnormal electrical pathway in the body. Radiofrequency (RF) energy may therefore be applied to biological tissue in proximity to tip assembly 212. Ablation procedures are typically used, for example, within the interior chambers of the heart to thermally ablate cardiac tissue. Electrode 208 may additionally be operated to record intracardiac signals and to provide pacing signals. It should be noted that tip assembly 212 is also suited for recording of intracardiac signals and to provide pacing signals. While formed as an integral unit, tip electrode 208 may include multiple electrode elements, such as ring electrodes for electrophysiological mapping purposes, spaced from one another by dielectric materials as is known in the art.

Figure 10:
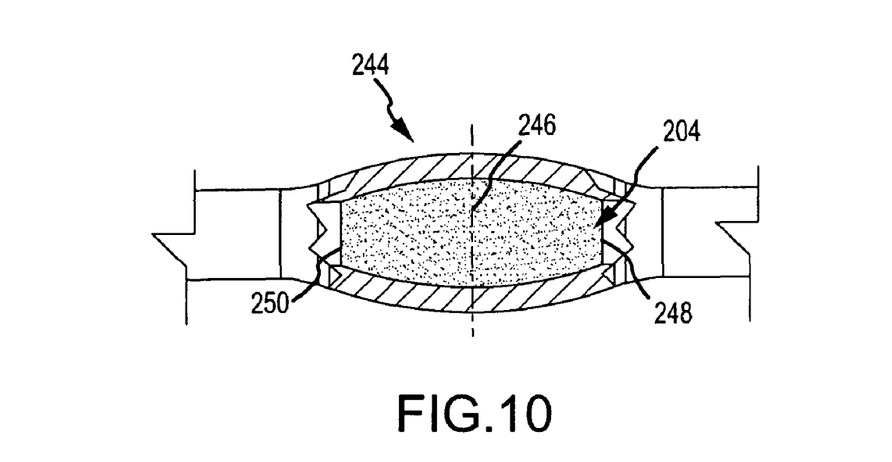
FIG. 10 illustrates a magnet assembly for the catheter shown in FIG. 7.

FIG. 10 illustrates a magnet assembly 244 for catheter 200 (shown in FIG. 7). Unlike magnets 106 and 108 (shown in FIG. 1) that are cylindrical in shape and have a constant outer diameter, magnet 204 is outwardly flared and has a generally ellipsoidal contour. That is, the outer diameter of magnet 204 is largest at an axial midpoint 246 and decreases from midpoint 246 to opposing ends 248, 250 of magnet 204, providing magnet 204 with a curved profile along an axial length of magnet 204.

In one embodiment, magnet 204 is encapsulated in sockets formed into adjacent tube portions as described above. Alternatively, magnet 204 is encapsulated in a sleeve that extends from the tube portions to cover magnet 204. Similarly to magnets 106 and 108, magnet 204 includes a central bore through which a tube passes. Magnet 204 is formed from, for example, neodymium-iron boron—45 (NdFeB-45) into the illustrated shape or an alternative shape. It should be understood that magnet 206 (shown in FIG. 7) may be formed in the same shape as or a different shape from magnet 204.

Figure 11:
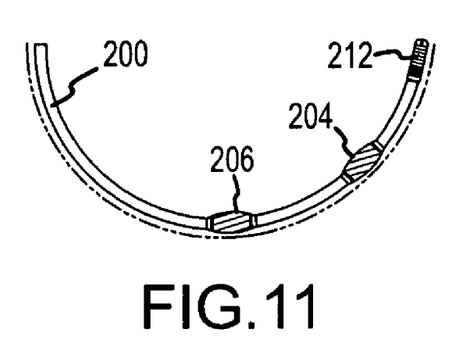
FIG. 11 illustrates a distal portion of the catheter shown in FIG. 7 in an operating position.

FIG. 11 illustrates a distal portion of catheter 200 in an exemplary operating position that shows the deflection of tip assembly 212 and magnets 204 and 206. By applying magnetic fields to magnets 204 and 206, and also positioning magnet 222 (shown in FIG. 7), the distal portion of catheter 200 may be precisely positioned at a specific location within the patient's body. The magnetic fields may be generated and controlled by, for example, a magnetic stereotactic system (not shown).

Figure 12:
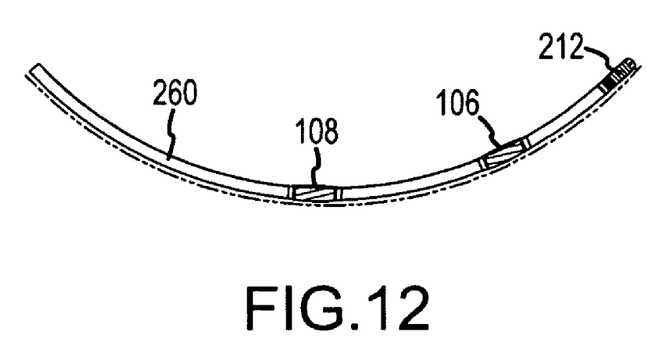
FIG. 12 illustrates a third exemplary embodiment of a distal portion of a magnetically guided catheter including a flexible tip and cylindrical magnets.

FIG. 12 illustrates a distal portion of an alternative catheter, such as a catheter 260. As illustrated, a distal portion of catheter 260 is shown in an exemplary operating position in which the deflection is caused by tip assembly 212 and magnets 106 and 108. By applying magnetic fields to magnets 106 and 108, and also positioning magnet 222 (shown in FIG. 7), the distal portion of catheter 260 may be precisely positioned at a specific location within the patient's body. The magnetic fields may be generated and controlled by, for example, a magnetic stereotactic system (not shown).

The external positioning magnets of catheters 100, 200, and 260 are believed to provide manufacturing benefits, and also performance benefits, in relation to conventional, and more complicated, catheter constructions for use with stereotactic systems. Larger positioning magnets are provided for increased magnetic response and performance, and tubing is used that is generally smaller in internal diameter than the magnets, thereby resulting in material savings in comparison to known catheters having larger tubing to accommodate the magnets. In addition, increased flexibility is provided. Sockets in the tubes encapsulate the external positioning magnets in a very manufacturable and generally low cost construction. The external positioning magnets that are separately provided from the electrode tips also reduce a complexity and parts count in the tip assembly relative to other known catheter tips providing comparable functionality.

Figure 13:
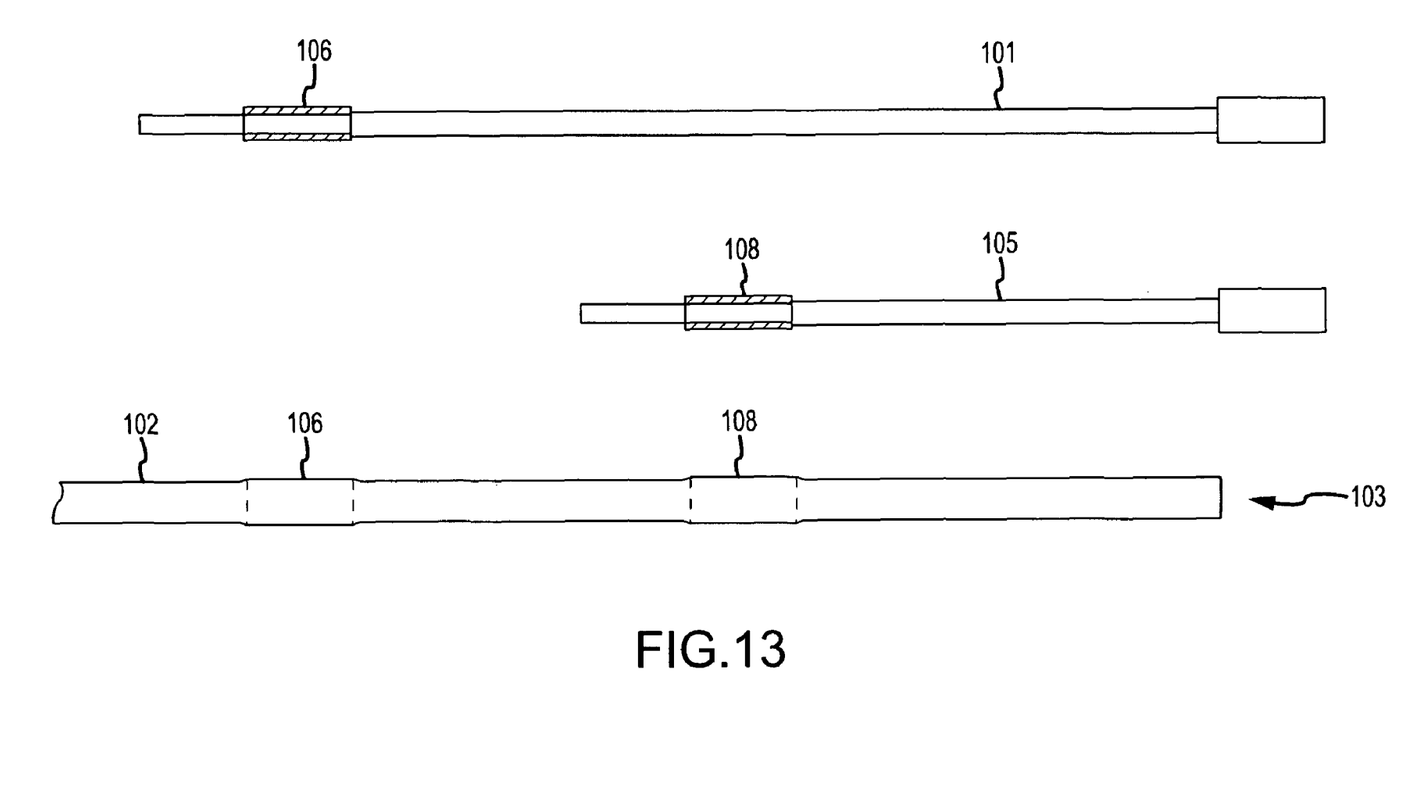
FIG. 13 illustrates an exemplary manufacturing process for the magnetically guided catheter.

FIG. 13 illustrates an exemplary manufacturing process for the magnetic guided catheter. Tubing 102 is a unitary tubing that is unitary in construction and formed as a single tubing prior to placing the magnets inside. In an exemplary embodiment, magnets 106 and 108 may be pushed into tubing 102 during the manufacture process in the direction illustrated by arrow 103. For example, magnets 106 and 108 may be positioned on mandrels 101 and 105, respectively, and pushed into tubing 102 one at a time using a lubricant such as, alcohol, to facilitate receiving magnets 106 and 108 therein. The alcohol conveniently evaporates after a short time. Magnets 106 and 108 are shown mounted on mandrels 101 and 105 outside of tubing 102. Magnets 106 and 108 are inserted into tubing 102 one at a time, by pushing mandrels 101 and 105 separately and sequentially in the direction of arrow 103.

According to this method, there may exist an interference fit between magnets 106 and 108, and tubing 102, thereby securing the position of magnets 106 and 108. It is noted that the drawings are exaggerated to better illustrate the interference fit. In reality, the interference fit may not be as pronounced as it is shown in the drawings. The interference fit may be formed by an outer diameter of the at least one magnet being larger than an inner diameter of the unitary flexible tubing. For example, the interference fit may be formed by magnets 106 and 108 having an outer diameter about 0.005 inches larger than the inner diameter of tubing 102.

In another exemplary embodiment, magnets 106 and 108 may be pushed into tubing 102 without any interference fittings. In this embodiment, tubing 102 may be wrapped in heat-shrink film or heat-shrink tubing. The heat-shrink process shrinks the heat-shrink film or tubing around tubing 102 so that the position of magnets 106 and 108 is secured within tubing 102.

Heat-shrink processes are well understood in the arts. For purposes of discussion, however, the process may implement any of a wide variety of commercially available heat shrink film or tubing. Magnets 106 and 108 are first positioned within the heat shrink tubing. The magnets are readily positioned while the heat shrink tubing is in an initial state (e.g., at room temperature) prior to processing. Optionally, the magnet may be pretreated with a coating, e.g., to reduce the effects of corrosion. Application of heat to the heat shrink film or tubing shrinks the film or tubing around magnets 106 and 108. Shrinkage of the tubing around the magnet applies the necessary pressure to maintain magnets 106 and 108 in the desired position within tubing 102 after the heat shrink film or tubing cools.

Also in exemplary embodiments, catheter 100 can be constructed to have different flexibilities along the length of tubing 102, particularly in the distal region where the magnets are placed. Typically, portion 126 (shown in FIG. 1) between the distal end (where the tip electrode is located) and first magnet 106 is desired to be the most flexible. Portion 124 between first magnet 106 and second magnet 108 disposed proximally from first magnet 106 is desired to have less flexibility. Still additional portions and additional magnets may be provided, with the proximal portions having less and less flexibility.

The flexibility can be determined by material properties and/or thickness. Thus, unitary tubing 102 can be made to have varying material properties along its length toward the distal end, so that the different portions will have different flexibilities. The shaft can also decrease in thickness toward the distal end. A thinner wall of tubing 102 results in greater flexibility, while a thicker wall of tubing 102 results in less flexibility.

Flexibility can change either continuously/gradually or in abrupt steps between the portions. The abrupt steps may be useful in defining the locations of the magnets, especially in the embodiment where the magnets are pushed into the shaft with a lubricant. As magnets 106 and 108 pass through different flexibility zones defined by abrupt steps, the abrupt change in flexibility provides tactile feedback that magnets 106 and 108 are passing from one flexibility zone to another.

The unitary construction of the flexible tubings of catheters 100 and 200 is believed to provide manufacturing benefits, and also performance benefits, in relation to conventional, and more complicated, catheter constructions for use with stereotactic systems. The catheter can be manufactured without requiring magnet-shaft fusion and without joints, ensuring high reliability and safety of the catheter. The unitary tubing is easier to manufacture, takes less time to manufacture, and does not require an expensive and complicated fusion machine. Eliminating the junction of the magnet and the shaft also reduces or altogether eliminates undesirable stiffness. In addition, the magnets that are separately provided from the electrode tips also reduces complexity and parts count in the tip assembly relative to other known catheter tips providing comparable functionality. The unitary flexible tubing may extend along substantially the entire length of the catheter body, and may have a distal end to be coupled to an electrode assembly and a proximal end to be coupled to a handle. Alternatively, the unitary flexible tubing may extend along a portion of the catheter body with no fused connections between the magnets, but may be attached to additional components to form the entire length of the catheter body. For example, the unitary flexible tubing containing the magnets with no fused connections may be fused with another flexible tubing to form the entire length of the catheter body.

While the invention has been described in terms of various specific embodiments, those skilled in the art will recognize that the invention can be practiced with modification within the spirit and scope of the claims.

What is claimed is:

1. A catheter comprising:
a flexible tubing having a proximal end and a distal end;
an electrode assembly attached to the distal end of the flexible tubing and including a first magnet therein, the electrode assembly including an electrically conductive tip electrode and an electrically nonconductive coupler which is connected between the tip electrode and the distal end of the flexible tubing, the coupler and the tip electrode being coupled by an interlocking connection; and
a second magnet spaced from the electrode assembly along a longitudinal axis of the tubing;
wherein the first magnet and the second magnet are responsive to an external magnetic field to selectively position and guide the electrode assembly within a body of a patient.

2. A catheter in accordance with claim 1, wherein the interlocking connection is formed by coupling an annular projection on the tip electrode and a groove on the coupler.

3. A catheter in accordance with claim 1, wherein the interlocking connection is a snap-fit connection.

4. A catheter in accordance with claim 1, wherein the first magnet is disposed in a cavity formed at least partially inside the coupler.

5. A catheter in accordance with claim 1, wherein the electrode assembly further includes a band electrode on an external surface of the coupler, the band electrode being spaced from the tip electrode.

6. A catheter in accordance with claim 1, wherein the first magnet includes an external groove forming a channel with the flexible tubing, the channel being oriented generally in a longitudinal direction.

7. A catheter in accordance with claim 1, further comprising a lumen passing through the first magnet and the second magnet, and in fluid communication with the electrode assembly, wherein the electrode assembly has at least one irrigation port.

8. A catheter in accordance with claim 1, wherein the flexible tubing comprises a plurality of sections, each section formed with an outwardly flared socket, and wherein the second magnet is positioned within the sockets of adjacent sections of tubing.

9. A catheter in accordance with claim 1, wherein the second magnet has an outer diameter greater than an outer diameter of the flexible tubing at a location spaced from the second magnet.

10. A catheter in accordance with claim 1, wherein the flexible tubing has a first outer diameter and a second outer diameter, the second outer diameter being greater than the first outer diameter and overlying the second magnet.

11. A catheter in accordance with claim 1, wherein the second magnet has one of a cylindrical shape and an ellipsoidal shape.

12. A catheter in accordance with claim 1, further comprising a third magnet separated from the second magnet by a first distance along the longitudinal axis of the flexible tubing, wherein the second magnet is spaced from the electrode assembly by a second distance along the longitudinal axis of the flexible tubing, the first distance being greater than the second distance.

13. A catheter in accordance with claim 1, wherein a portion of the flexible tubing distal to the second magnet is more flexible than another portion of the flexible tubing proximal to the second magnet.

14. A catheter in accordance with claim 1, wherein the flexible tubing is a unitary tubing, and wherein the second magnet is placed inside the flexible tubing after the unitary flexible tubing is formed.

15. A catheter in accordance with claim 14, wherein the second magnet is pushed into the unitary flexible tubing with an interference fit therebetween.

16. A catheter in accordance with claim 14, wherein the second magnet is placed inside the unitary flexible tubing and the unitary flexible tubing is heat-shrunk over the second magnet.

17. A catheter comprising:
a flexible tubing having a proximal end and a distal end;
an electrode assembly attached to the distal end of the flexible tubing and including a first magnet therein, the electrode assembly including an electrically conductive tip electrode and an electrically nonconductive coupler which is connected between the tip electrode and the distal end of the flexible tubing; and
a second magnet spaced from the electrode assembly along a longitudinal axis of the tubing;
wherein the flexible tubing is a unitary tubing, and wherein the second magnet is placed inside the flexible tubing after the unitary flexible tubing is formed;
wherein the first magnet and the second magnet are responsive to an external magnetic field to selectively position and guide the electrode assembly within a body of a patient.

18. A catheter in accordance with claim 17, wherein the second magnet is pushed into the unitary flexible tubing with an interference fit therebetween.

19. A catheter in accordance with claim 18, wherein alcohol as a lubricant is provided between the second magnet and the unitary flexible tubing.

20. A catheter in accordance with claim 17, wherein the second magnet has an outer diameter which is larger than an inner diameter of the unitary flexible tubing.

21. A catheter in accordance with claim 17, wherein the second magnet is placed inside the unitary flexible tubing and the unitary flexible tubing is heat-shrunk over the second magnet.

22. A catheter in accordance with claim 17, wherein a portion of the unitary flexible tubing distal to the second magnet is more flexible than another portion of the flexible tubing proximal to the second magnet.

23. A catheter in accordance with claim 22, wherein the portion of the unitary flexible tubing distal to the second magnet is thinner than the portion of the flexible tubing proximal to the second magnet.

24. A catheter in accordance with claim 22, wherein the portion of the unitary flexible tubing distal to the second magnet includes a material which is more flexible than a different material in the portion of the flexible tubing proximal to the second magnet.

25. A catheter in accordance with claim 17, wherein the first magnet is disposed in a cavity formed at least partially inside the coupler.

26. A catheter in accordance with claim 17, further comprising a lumen passing through the first magnet and the second magnet, and in fluid communication with the electrode assembly, wherein the electrode assembly has at least one irrigation port.

27. A catheter in accordance with claim 17, further comprising a third magnet spaced proximally from the second magnet along the longitudinal axis of the unitary flexible tubing, the magnets being responsive to an external magnetic field to selectively position and guide the electrode assembly within a body of a patient.

28. A catheter in accordance with claim 27, wherein the second magnet is spaced from the first magnet by a first distance along the axis of the unitary flexible tubing, and the third magnet is spaced from the second magnet by a second distance along the axis of the tubing, wherein the second distance is greater than the first distance.

29. A catheter in accordance with claim 17, wherein the unitary flexible tubing has a proximal end and a distal end defining substantially an entire length of the catheter.

* * * * *